United States Patent
Morganti et al.

(10) Patent No.: US 8,552,164 B2
(45) Date of Patent: Oct. 8, 2013

(54) SPRAY-DRIED CHITIN NANOFIBRILS, METHOD FOR PRODUCTION AND USES THEREOF

(75) Inventors: Pierfrancesco Morganti, Aprilia Lt. (IT); Corrado Muzzarelli, Ancona An (IT)

(73) Assignee: Mavi Sud S.r.l., Aprilia (IT)

( * ) Notice: Subject to any disclaimer, the term of this patent is extended or adjusted under 35 U.S.C. 154(b) by 995 days.

(21) Appl. No.: 12/094,912

(22) PCT Filed: Nov. 23, 2006

(86) PCT No.: PCT/IB2006/054403
§ 371 (c)(1),
(2), (4) Date: Sep. 4, 2008

(87) PCT Pub. No.: WO2007/060628
PCT Pub. Date: May 31, 2007

(65) Prior Publication Data
US 2009/0203642 A1  Aug. 13, 2009

(30) Foreign Application Priority Data
Nov. 23, 2005 (IT) .............. RM2005A0585

(51) Int. Cl.
*C08B 37/08* (2006.01)
*C07H 5/06* (2006.01)
*C07H 1/00* (2006.01)
*A01N 43/04* (2006.01)

(52) U.S. Cl.
USPC ............ 536/20; 536/55.3; 536/124; 514/55

(58) Field of Classification Search
USPC .............. 536/20, 55.3, 124; 514/55
See application file for complete search history.

(56) References Cited

U.S. PATENT DOCUMENTS

| | | | |
|---|---|---|---|
| 4,699,135 A | 10/1987 | Motosugi et al. | |
| 6,602,994 B1 * | 8/2003 | Cash et al. | 536/30 |
| 6,638,918 B2 | 10/2003 | Davison et al. | |
| 2003/0104020 A1 | 6/2003 | Davison et al. | |
| 2008/0118563 A1 | 5/2008 | Muzzarelli et al. | |

FOREIGN PATENT DOCUMENTS

| | | | |
|---|---|---|---|
| EP | 0 171 254 | | 2/1986 |
| JP | 2003055232 A | * | 2/2003 |
| KR | 2005032656 A | * | 4/2005 |
| WO | 00/47628 | | 8/2000 |
| WO | 03/042251 | | 5/2003 |
| WO | 2004/078790 | | 9/2004 |
| WO | 2006/048829 | | 5/2006 |

OTHER PUBLICATIONS

International Search Report for PCT/IB2006/054403, May 2, 2007.
Int'l Prel. Report on Patentability for PCT/IB2006/054403, May 2, 2007.
Min et al. "Chitin and chitosan nanofibers: Electrospinning of chitin and deacetylation of chitin nanofibers" Polymer 45:7137-7142 (2004).
Zussman et al. "Failure modes of electrospun nanofibers" Appl. Phys. Lett. 82:3958-3960 (2003).
Lu et al. "Morphology and properties of soy protein isolate thermoplastics reinforced with chitin whiskers" Biomacromol. 5:1046-1051 (2004).
Nair et al. "Crab shell chitin whisker reinforced natural rubber nanocomposites. 1. Processing and swelling behavior" Biomacromol. 4:657-665 (2004).
Persson et al. "Single crystals of α-chitin" Int. J. Biol. Macromol. 14:221-224 (1992).

* cited by examiner

*Primary Examiner* — Patrick Lewis
*Assistant Examiner* — Everett White
(74) *Attorney, Agent, or Firm* — Nixon & Vanderhye PC

(57) ABSTRACT

The invention relates to a novel method for production of nanofibrillar chitin, sustainable from an industrial manufacturing standpoint and suitable for producing chitin nanofibrils having improved properties and free from less crystalline components. The invention also relates to novel chitin nanofibrils obtained with said method and characterized by an increased dispersibility in aqueous media. The invention further relates to uses of nanofibrils in pastes and aqueous gels useful for topical on-skin application, to the manufacturing of materials of biomedical interest, as well as to the deposition of chitin nanofibrils on coating surfaces or the incorporation of the same inside of items like, e.g., fibers and fabrics of any Origin, natural as well as synthetic or mixed ones.

17 Claims, 5 Drawing Sheets

SPRAY-DRIED CHITIN NANOFIBRILS, METHOD FOR PRODUCTION AND USES THEREOF

This application is the U.S. national phase of International Application No. PCT/IB2006/054403, filed 23 Nov. 2006, which designated the U.S. and claims priority to Italy Application No. RM2005A000585, filed 23 Nov. 2005; the entire contents of each of which are hereby incorporated by reference.

TECHNICAL FIELD OF THE INVENTION

The invention relates to a novel method for production of nanofibrillar chitin, sustainable from an industrial manufacturing standpoint and suitable for producing chitin nanofibrils having improved properties and free from less crystalline components. The invention also relates to novel chitin nanofibrils obtained with said method and characterized by an increased dispersibility in aqueous media. The invention further relates to uses of nanofibrils comprising formulation of pastes and aqueous gels useful for topical on-skin application, to the manufacturing of materials of biomedical interest, as well as to the deposition of chitin nanofibrils on coating surfaces or the incorporation of the same inside of items like, e.g., fibers and fabrics of any origin, natural as well as synthetic or mixed ones.

STATE OF THE PRIOR ART

Prior experimentation indicated the usefulness of nanofibrils as reinforcing material in textile fibers poly(ethylene oxide) poly(propylene oxide) and poly(caprolactone) (Morin & Dufresne, 2002) and other polymer materials like soy (Lu et al., 2004), poly(vinyl alcohol) (Sriupayo et al., 2005), rubber (Nair & Dufresne, 2003), and thermoplastics (styrene with butyl acrylate) (Paillet & Dufresne, 2001) i.e. solid composites only mechanically characterized.

Chitin, native in crustaceans, is a microfibrillar material in alpha polymorphic form, having small chitin deacetylation rate (about 0.05) given by chitin deacetylase enzyme with the aim of binding it to proteins during biosynthesis. After having been secreted in amorphous form, chitin becomes fibrous and crystalline, in particular generating chitin crystallites also called nanofibrils or whiskers. In vitro, the partial acid hydrolysis occurs more rapidly on the less crystalline parts of the chitin fibers, thereby freeing the nanofibrils; these are rigid, resistant items of 250 nm in average length, with a rectangular section of about 7×20 nm. The surface of 1 g nanofibrils is of 180 m$^2$. They behave like colloids, as not settling (sedimenting) from their suspensions, and spontaneously separate into isotropic and anisotropic phases, the second one being nematic; they reciprocally recognize each other, arranging in an orderly manner, originating optical phenomena typical of liquid crystals, and exhibit positive zeta potential values as a consequence of their partial cationic character.

Nanofibrils in aqueous suspension are sensitive to the presence of organic solvents, dyes and metal ions or electrolytes in general that, by disturbing the blanket of water molecules surrounding them, cause precipitation from the suspensions. All the more so, heat treatments lead to aggregation, even irreversible, of the nanofibrils.

Also known are chitin nanofibrils from *Thalassiosira fluviatilis* (diatom), *Riftia pachiptila* (sea worm), and from *Lamellibranchia tatsuma*. Analogously, cellulose nanofibrils are known.

The above has been observed by various authors, who understood nanofibrils usefulness to elucidate chitin structure by X-ray spectrometry, and described various processes for isolating very modest amounts of nanofibrillar chitin from various organisms.

It is known in the current state of the art that nanofibrils preparation is performed in accordance with the method described with variants by Belamie et al (2004)) and by other preceding authors (Persson et al (1992), Revol et al (1993, 1996), Li et al (1996), comprising the following steps:

Boiling chitin powder in 3 M hydrochloric acid for about 1.5-3 hours, with a chitin/acid solution weight ratio of about 1:10-1:30.

Adding large amounts of water in successive dilution and centrifugation cycles until rising of pH values (pH 2), at which the colloidal chitin suspension appears. In general, this process is carried out with 12.000 rpm centrifuges that abate suspensions and allow to remove hot water, over at least 3 cycles, replacing it with ultrapure water.

It has been observed that this process implies a weight loss of about the 40%, due to the hydrolytic dissolution of less crystalline parts of chitin.

Moreover, depending on concentration of nanofibrils in suspension and hydrolysis time, spontaneous phase separation phenomena can occur: i.e., at +24 hours at room temperature a 5% suspension yields an (inferior) anisotropic phase and a (superior) isotropic phase.

However, any chemical perturbation of the electrical double layer existing about the individual nanofibril (weak polycation) leads to precipitation of a prevailing fraction of chitin.

Nanofibrils are not dried in order to preserve them, and to their suspensions it is added sodium azide as antimicrobial.

Alternative techniques for obtaining chitin nanofibrils from colloidal suspensions make use of drying (Revol et al, 1993; Nair et al, 2003) or lyophilizing (Persson et al, 1992) procedures.

Evidently, the method of preparing nanofibrils described by Belamie, though useful for small quantities intended for basic studies, is not susceptible of being extended to scaled-up preparations due to the following reasons:

1. The removal/dilution of 3 M HCl effected by addition of water and successive decanting entails handling large masses of water (hundreds of times the weight of chitin), and introduces lengthy waiting times due to the required settling of the particles (not yet colloidal nanofibrils at pH<2).

2. The precipitation of suspensions by ultracentrifugation in incompatible with usual industrial options. In fact, nanofibrils settle at 12.000 rpm, whereas industrial centrifuges do not exceed 7000 rpm.

3. Depending on authors, ultrasounds are applied to perform or speed up dispersion at certain stages of the process. Sonication is not easy to apply to large masses and generates an enormous amount of heat, uncontrollably raising the temperature.

4. The overall yield is merely of about the 20%, as a certain amount of chitin powder (albeit fine) is neither hydrolyzed nor reconduced to nanofibrils, and is discarded.

5. Lastly, the procedures of isolating nanofibrils from colloidal suspensions, and of drying, generate aggregation of the nanofibrils, which therefore become difficult to redisperse at the moment of use. For instance, evaporation produces rigid films of ordered nanofibrils, whereas lyophilization produces highly dehydrated powders, them also prone to difficult redispersion; analogously, insolubilization with solvents such as alcohols deprives nanofibrils of the water layer covering them, generating aggregates. Even plasticizers like glycerol and sorbitol are not capable of fully preventing the aggregation phenomenon.

Scope of the present invention is to provide a solution to the problems left unsolved by known processes, above all to that of the difficult applicability at an industrial level of the known methods and that of the difficult redispersion in aqueous medium of the nanofibrils produced with known methods.

SUMMARY OF THE INVENTION

The solution to the problem of scaling-up the production of chitin nanofibrils is singled out in a novel process based on an approach opposite with respect to that of known methods. While known methods imply successive sedimentation cycles for the nanofibrils, through ultracentrifugation and resuspension in a novel medium, the method of the invention instead provides for nanofibrils to always remain in suspension, whereas larger-sized (coarser) particles are sedimented with a normal centrifuge. Chitin nanofibrils in colloidal suspension are finally recovered in a dried form through a spray-drying technique, instead of through ultracentrifugation and/or evaporation or lyophilization or drying over phosphorus pentoxide.

It has surprisingly been observed that, with respect to those produced with known methods, the chitin nanofibrils obtained through this process exhibit novel and original chemico-physical properties.

Hence, in light of the foregoing, a first object of the invention is a method for production of chitin nanofibrils comprising the steps of subjecting a suspension of chitin nanofibrils to drying through spray-drying technique and recovering the so obtained nanofibrils.

In particular, the suspension of chitin nanofibrils is produced through a process comprising the steps of: a) subjecting the powder chitin tel quel to boiling in a concentrated strong acid; b) settling the solid and the removing acid supernatant; c) dialyzing in water and resuspending in water the solid; d) centrifuging the suspension produced during the dialysis; e) separating the solid residue containing non-hydrolyzed chitin particles from the suspension of nanofibrillar chitin intended for the spray-drying step; and f) optionally, subjecting again the solid residue yielded from centrifugation to the entire cycle.

A second object of the invention are the spray-dried chitin nanofibrils obtained through the method of the invention, in particular nanofibrils exhibiting the characteristics of having a crystallization water content ranging from 5 to 10% and a hydration state ranging from 10 to 15%, which are capable of instantaneously dispersing in water and of forming stable suspensions in an aqueous or organic medium. They may have an IR spectrum as shown in FIG. 1 and an X-diffraction spectrum as shown in FIG. 2.

A third object of the invention are stable suspensions of chitin nanofibrils in an aqueous or organic, fluid or viscous medium.

A fourth object of the invention are the spray-dried chitin nanofibrils for use in a therapeutic, surgical or cosmetic treatment, in particular in protective or curative treatments of skin abrasions, wounds, burns, or in treatments for supporting and stimulating haemostasis, healing and regeneration processes of injured tissues, or in dermocosmesis treatments through subcutaneous hypodermic injection thereof or cutaneous application thereof with masks, films or sponges.

A fifth object of the invention are compositions comprising the chitin nanofibrils in a form selected from (dry) solid state, aqueous or organic liquid suspension, gel, paste, or other form suitable for application on skin or mucosae and a pharmaceutically or cosmetically acceptable excipient, optionally comprising further components selected from thickeners, plasticizers, emulsifiers, preservatives, bactericides, fungicides, antimicrobials, immunomodulants, metal ions, alpha-amino acids, beta-amino acids, carotenoids or antioxidants of any origin, sun filters, vegetal extracts, moisturizers, derivatives or mixtures thereof and other active principles of known pharmacological activity.

Further objects of the invention are articles selected from films, sponges, synthetic or natural fabric, comprising there-inside or adsorbed on their surface the spray-dried chitin nanofibrils, or containers comprising the spray-dried chitin nanofibrils and equipped with means for intra/subcutaneous or topical application.

Other further objects of the invention are fibers, fabrics or films incorporating the spray-dried chitin nanofibrils and having synthetic or semisynthetic nature, optionally comprising further biologically active substances like silver ions; and natural yarns or fabrics treated with the spray-dried chitin nanofibrils and optionally comprising further biologically active substances, like silver ions, attached on the chitin nanofibrils.

Lastly, object of the invention is again the use of spray-dried chitin nanofibrils as metal ion chelating agents or as slow-release agents of drugs or other active principles.

The invention provides several advantages. The type of centrifuge employed is a common 3000 rpm centrifuge, instead of being the 20.000 rpm ultracentrifuge. Industrial spray-drying systems are faster and less expensive with respect to industrial lyophilizers; process times are markedly shortened, lengthy settlings (sedimentations) and several dilutions being avoided. Recycling of the residual chitin, recovered from the settled fraction, raises the yield up to 60%, as said residue is fully hydrolyzed at the second treatment.

Lastly, the nanofibrils thus yielded possess a content of crystallization water and adsorbed water allowing their instantaneous and homogeneous redispersion in water. Therefore, they may be stored indefinitely as dry powder at room temperature and humidity. Moreover, the nanofibrils of the invention attain crystallinity levels unattained by nanofibrils obtained with the known methods; this characteristic reverberates in IR and X-diffraction spectra different from those of the nanofibrils described in literature.

DETAILED DESCRIPTION OF THE INVENTION

Figure 1:
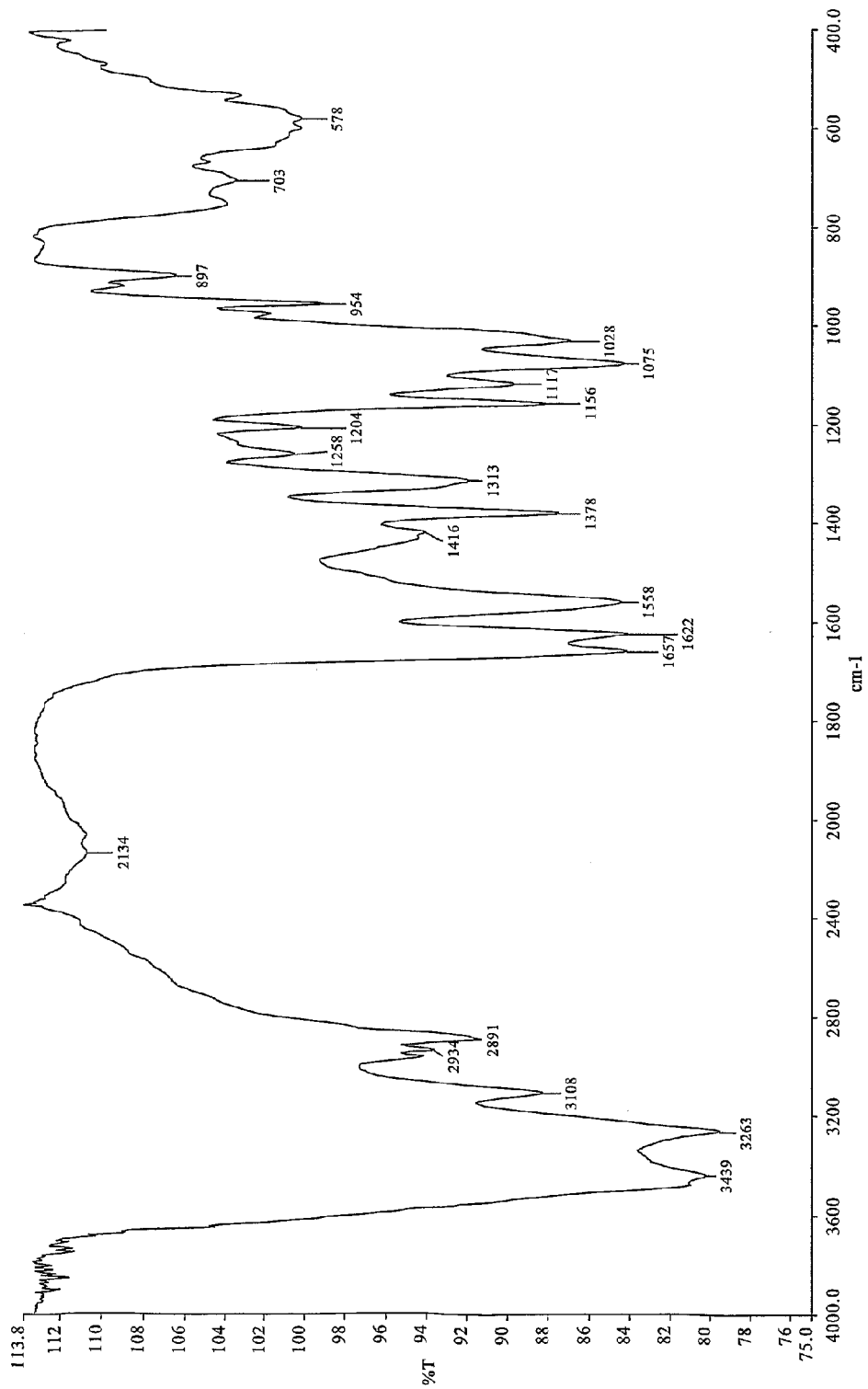
FIG. 1 illustrates the IR spectrum of the spray-dried chitin nanofibrils of the invention. The high crystallinity of the nanofibrils reverberates in the high resolution of the spectrum, highlighting bands practically indistinguishable in the spectra of nanofibrils obtained with known methods. In particular, the bands at 1204, 975 and 917 $cm^{-1}$ and a sequence of distinctly resolved small bands from 3855 to 3652 $cm^{-1}$.

The starting product for the compounds of the invention is crustacean chitin, for instance crab alpha-chitin, commercially available in the form of powder or flakes. Other types of chitin may be used as well.

Pilot-scale production of spray-dried chitin nanofibrils opens new perspectives to applications, considering that known applications to date are purely theoretical owing to product scarcity and to the incomplete definition of its grade. The present invention not only describes a novel method for production, but also novel chitin nanofibrils that, having been obtained by spray-drying, are susceptible of being brought into suspension in aqueous and organic environments and stably kept over long times. These features, i.e. the high dispersibility and stability of the suspensions obtained, paves the way to numberless practical applications.

Process for Production of Chitin Nanofibrils:

In a first step of the process, chitin powder is boiled under reflux with stirring in a strong acid, preferably 3 M HCl, for a sufficient time, usually of 90 min: after a brief rest, chitin settles spontaneously and it is easy to remove nearly all of the supernatant acid with a pump.

In a second step, it is added a water volume equal to that of the acid removed, and the resulting suspension is dialyzed against water for a 20-hour time, or treated by hollow fiber ultrafiltration according to techniques known to those skilled in the art.

Then, the suspension is centrifuged at a low number of rpm (about 3000) with a standard centrifuge to remove non-hydrolyzed chitin particles, whereas nanofibrils remain in suspension. The centrifugation yields: a solid chitin powder residue, intended to be subjected to further treatment as in the first step, and the colloidal suspension of chitin nanofibrils intended for the subsequent spray-drying treatment. The above-mentioned solid chitin powder residue, discarded by the preceding authors, proved particularly sensitive to a second treatment with fresh 3 M HCl, in which it is nearly totally transformed into nanofibrils.

The colloidal suspension of nanofibrils, preferably obtained by reuniting the first suspension with that produced by recycling the solid residue, is pumped through the sprayer at about 150° C. for a few seconds, and immediately cooled to about 40° C. Dry product yield is about 60% of the theoretical one.

Spray-Dried Chitin Nanofibrils

High inlet temperature (about 150° C.) notwithstanding, it has surprisingly been found that the nanofibrils thus produced undergo minimal alteration of their water sphere and of the crystallization water, as exposure to that temperature is very short. In fact, the spray-dried nanofibrils are characterized by a crystallization water content ranging from 5 to 10% and a hydration state ranging from 10 to 15%.

Thanks to these characteristics, the nanofibrils of the invention, though rolled up into structures resembling microspheres, are not aggregated and spontaneously redisperse in water even after months of storage in a closed container.

Thermogravimetric curves recorded on such samples demonstrate a different and more favourable hydration state compared to known lyophilized or hot-dried nanofibrils described in the prior art. Analytical and control methods required for implementing the invention and identifying and characterizing the nanofibrillar chitin are: infrared (IR) spectrophotometry, X-diffraction spectrometry, thermogravimetry and electron microscopy.

Figure 3:
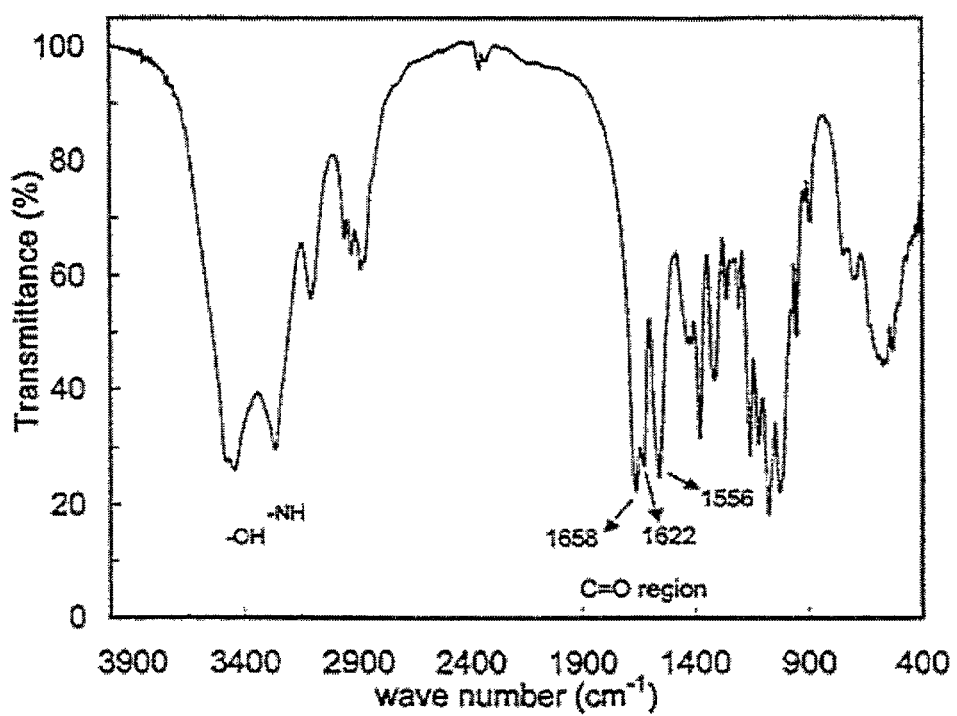
FIG. 3 illustrates the IR spectrum of the chitin nanofibrils obtained with the known method described by Nair, Dufresne, Biomacromolecules, 4, 660 (2003).
Figure 4:
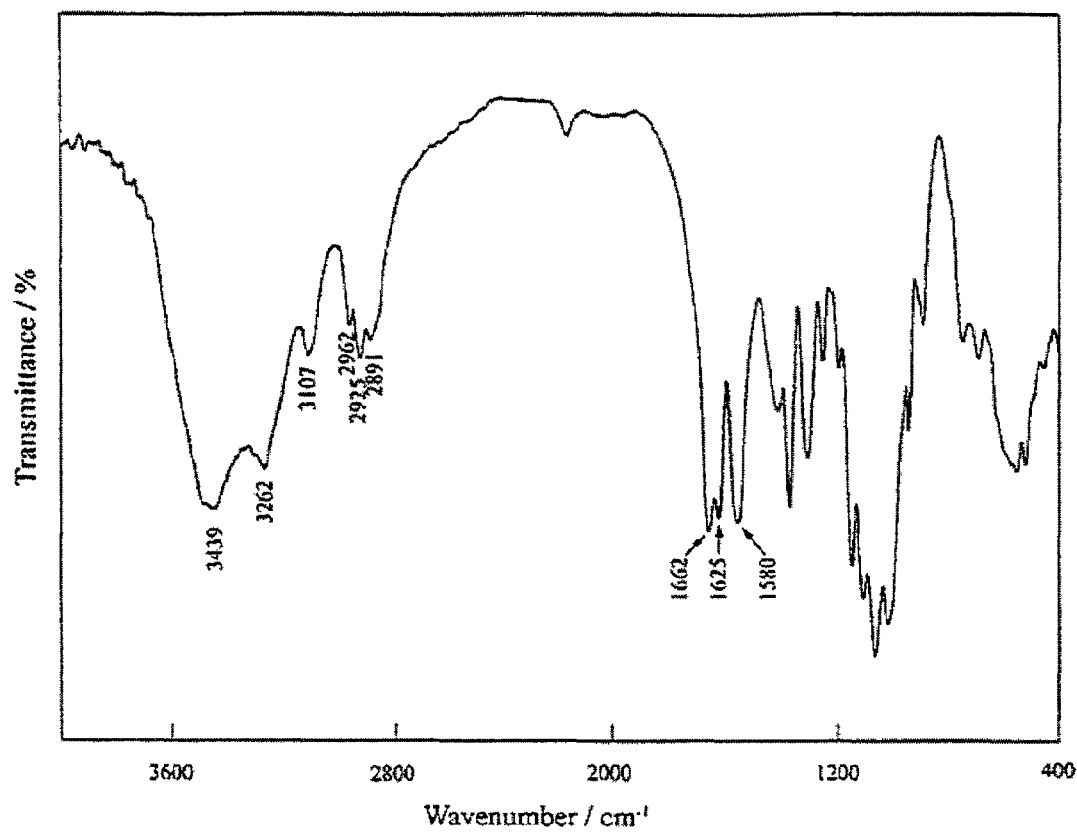
FIG. 4 illustrates the IR spectrum of the chitin nanofibrils obtained with the known method described by Lu et al. Biomacromolecules, 5, 1048 (2004).
Figure 5:
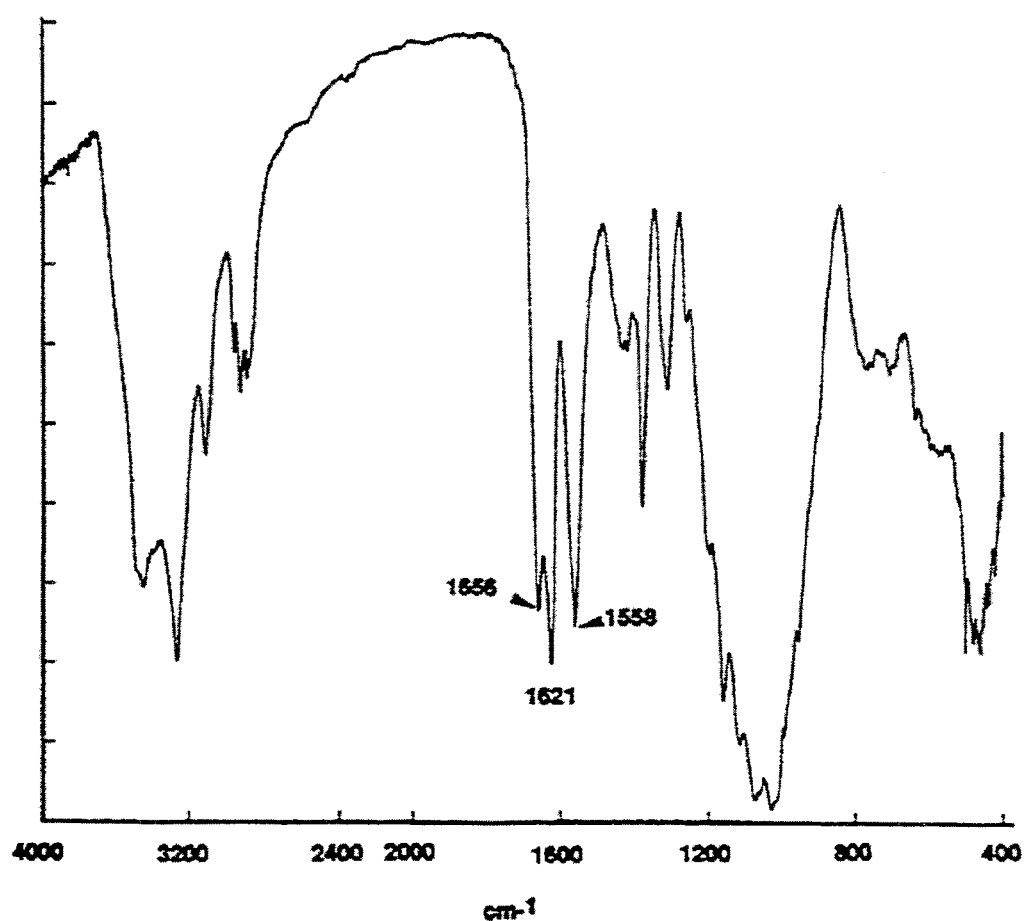
FIG. 5 illustrates the IR spectrum of the chitin nanofibrils obtained with the known method described by Persson et al. Int. J. Biol. Macromol. 14, 223, (1992).

The IR spectra of chitin nanofibrils contain all of the bands characteristic of chitin with the due intensity, in particular those at 1556, 1622, 1658, 2891, 3107, 3262 and 3439 $cm^{-1}$, as shown by Nair & Dufresne (2003), Lu et al. (2004) and Persson et al. (1992). However, the chitin nanofibrils produced by the present method are more crystalline than those produced to date for analytical purposes. In fact, by comparing the spectrum in FIG. 1 with the spectra published by the cited authors (FIGS. 3, 4 and 5), it is evident that in former several bands are present that are indistinguishable in the spectra of the preceding authors, exactly those at 1204, 975, 917 $cm^{-1}$. Moreover, the bands at 1156, 1116, 1075 and 1029 $cm^{-1}$ are well-resolved, whereas in the preceding spectra they are hazy. Even the two most important bands qualifying the chitin as alpha, i.e. the bands at 1656 and at 1622 $cm^{-1}$, are much more definite and resolved. Lastly, the signals in the 3855-3652 $cm^{-1}$ range indicate an improved hydration state.

The dimensions of the nanofibrils are assessed through transmission electron microscopy (TEM) technique, by means of an image analyzer and the drafting of a histogram showing length distribution: the 250-nm length is present in 25% of the nanofibrils; the 200-nm one in 23% thereof, the 300-nm one in 18% thereof, etc., with maximum values of 450 nm for 3% thereof. The measuring of the degree of crystallinity of the nanofibrils obtained is carried out through X-ray diffraction spectrometry technique, and this is correlated to the area subtended by the diffraction peaks. The values of the nanofibrils of the invention, reported in FIG. 2, are summarized in the following table:

| d, nm | 0.962 | 0.704 | 0.469 | 0.344 |
|---|---|---|---|---|
| 2θ, degrees | 9.3 | 12.7 | 19.0 | 25.6 |

Figure 2:
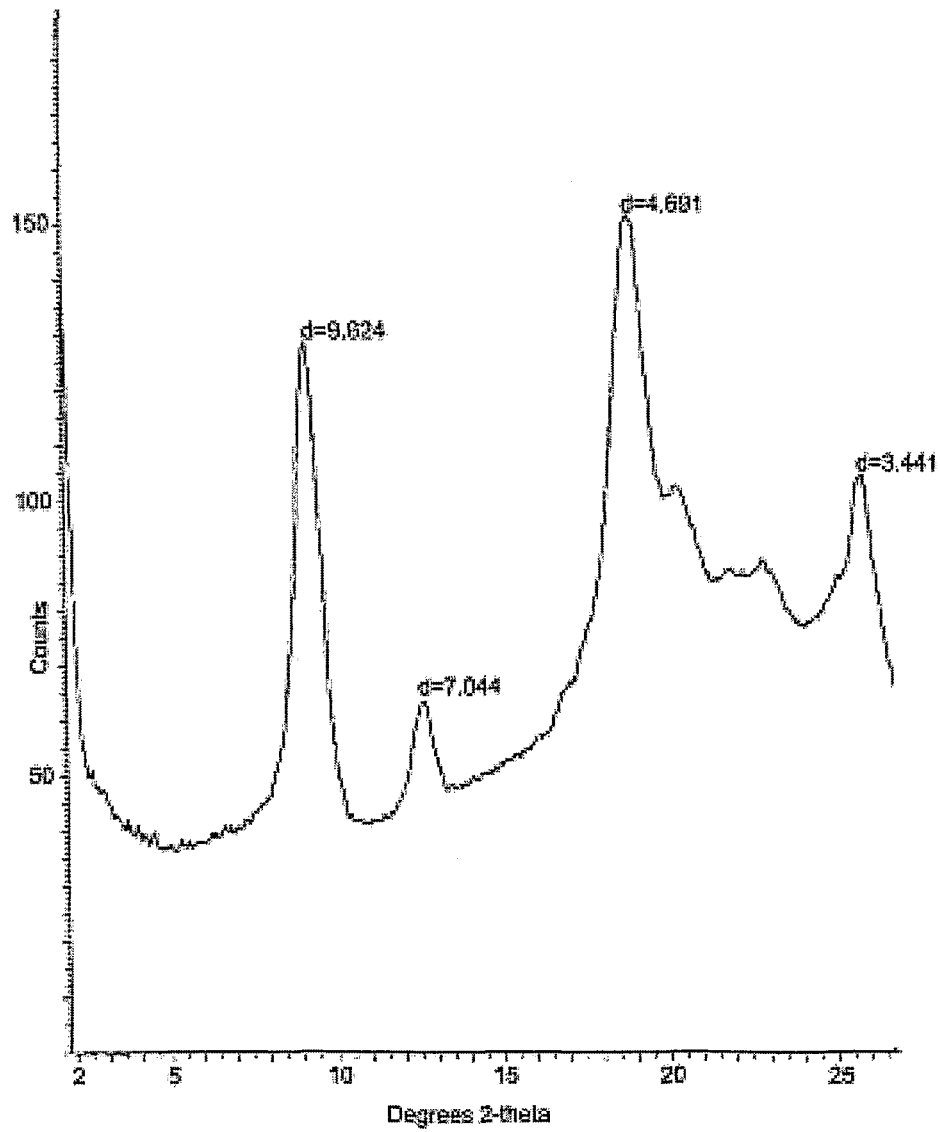
FIG. 2 illustrates the X-diffraction spectrum of spray-dried chitin nanofibrils (values in Angstrom).

In particular, the spectrum in FIG. 2 indicates that the nanofibrils produced by the present method are highly crystalline, as peaks are present that in normal chitin samples are depressed or scarcely evident, in particular those at 0.7044 and 0.3441 nm. The other two major peaks are of strong intensity and well-defined.

Lastly, thermogravimetry by suitable programmed-temperature balance allows to detect in derivative thermograms first the water released in the 70-180° C. range, and the reading of the temperature (near to 300° C.) at which pyrolysis starts.

Cosmetic and Therapeutic Applications

The spray-dried nanofibrils of the invention instantaneously yield highly homogeneous dispersions. Surprisingly, this characteristic was detected, for the first time, also in connection with suspensions of nanofibrils in viscous aqueous solutions, of which the nanofibrils can enhance the biological properties without increasing the viscosity—in fact, an excessive increase of the latter would prejudice their use. As the chitin nanofibrils of the invention exhibit an enormous surface development, allowing them to interact with enzymes, platelets and other compounds or cells present in living tissues, addition of nanofibrils of the invention to viscous solutions accordingly increases the content of biochemically active material without restricting its practical applicability. The spray-dried chitin according to the invention keeps all general properties of chitin. It is highly biocompatible with human tissues, is not recognized as an extraneous body; is biodegradable, as already highlighted by works with films of chitin implanted in rat's back; or as suture thread; is slowly reabsorbable also in human tissues by means of lysozime; influences collagen's proline-hydroxyproline ratio; fosters proliferation of fibroblasts, collagen producers; is not antigenic, instead fostering the organism's immunologic response; is a haemostatic agent; following intravenous administration as a thin-particle suspension causes fagocytosis by macrophages.

Moreover, the suspensions of spray-dried chitin form, after removal of dispersion liquids, resistant, reabsorbable and tissue-compatible films.

Thanks to these numberless properties, the spray-dried chitin nanofibrils have medical-surgical, generally clinical and cosmetic-dermatological applications.

In particular, they find application in a protective or curative treatment of skin abrasions, wounds, burns, particularly in a treatment for supporting and stimulating hemostasis, tissue healing and regeneration processes of injured tissues.

Moreover, the compositions of the invention find application in the cosmetic surgery field, in particular in the dermocosmesis field, as cutaneous fillers for the treatment of wrinkles and other cutaneous irregularities and blemishes through subcutaneous hypodermic injection, or in the cutaneous treatment through masks, films, sponges.

In the use as cutaneous filler, the compositions of the invention, with the due technical skills, can be used in association with other natural and synthetic biocompatible polymers, like, e.g., hyaluronic acid, polylactic (PLA) or polyglycolic (PGA) acid with copolymers thereof (PLGA) or with other biomimetic hydrogels such as polyethylene glycols (PEGs) or oligo-polyethylene glycol fumarate (OPF), etc.

Suitable pharmaceutical or cosmetic compositions comprise the spray-dried nanofibrils in a dry state, or liquid, fluid or viscous suspensions, gel, paste, or any other form allowing a practical topical application on skin or mucosae.

The suspensions of nanofibrils may contain thickeners or plasticizers, like glycerol, sorbitol, mannitol or other polyols, chitosan, chitosan glycolate, hydroxymethylglycinate, hydroxyethyl cellulose or dibutyryl chitin.

A practical embodiment of the present invention is a fluid or viscous gel of chitosan to be used as liquid dressing or tissue-healing antibacterial and antifungal even in the form of spray, in which there are suspended chitin nanofibrils that, without increasing the viscosity, greatly increase the chitin/chitosan content in terms of weight percent.

The suspensions of nanofibrils of the invention are placed into containers equipped with devices or means for both an intra/subcutaneous application, e.g. hypodermic syringes, and a topical one on-skin or on mucosae: e.g., spray cans, nebulizers, pencils, brushes or other usual means capable of depositing on-skin a liquid thin layer, which, after drying, generates a film of material, protective and absorbable over time, to protect wounds, abrasions, irritations or burns. The spray form is particularly suitable for the treatment of large-sized wounds or burns. Moreover, the fact that chitin nanofibrils possess weak cationic character, enables to adsorb them on spongy surfaces or on films having anionic character, e.g. modified cellulose like carboxymethyl cellulose, or polyacrylate, or on natural yarns like wool, cotton, flax, hemp, jute, or synthetic yarns.

Suchlike articles treated with suspensions of nanofibrils are susceptible of dermocosmetic use by means of face masks or fabrics in general, which, into contact with skin, prevents forms of allergy and/or allergic sensibilization.

These articles differ from those described in the prior art, as the former do not incorporate chitin nanofibrils thereinside, rather having the surface covered with nanofibrils.

Optionally, the compositions of the invention may also contain bactericides, fungicides, antimicrobials like, e.g., chlorhexidine hydrochlorate, triclosan, or metallic silver or other antimicrobials of different nature, alpha-amino acids, beta-amino acids or derivatives thereof like taurine, carotenoids, such as lutein, moisturizers, such as glycine and other pharmacologically active principles. Suspensions of spray-dried chitin nanofibrils containing these substances can generate, by evaporation of the aqueous phase, mechanically resistant films used as cosmetic beauty masks or for various medical uses.

In-Film Incorporation of Spray-Dried Chitin Nanofibrils and Synthetic, Semisynthetic and Natural Polymer Fibers.

A further application of the spray-dried chitin nanofibrils relates to the manufacturing of films, fibers and other solid items. Incorporation of nanofibrils is carried out through known techniques, i.e. spinning (melt-spinning, dry-spinning or wet-spinning), extrusion (coextrusion, film-making from solutions, calendering) and hot-forming.

Prior art chitin in the form of granules, though fine-sized, is scarcely compatible with generally hydrophobic synthetic polymers, and tends to agglomerate in the extruder, forming globules. On the contrary, the spray-dried chitin nanofibrils suitably mixed to the mass being heated and melt, arrange themselves more evenly, generating a homogeneous and stable dispersion. Contents of spray-dried chitin nanofibrils, up to 70% by weight, are added to polymers like: polyhydroxybutyrate, polyhydroxybutyrate-covalerate, polylactic, polyglycolic, poly-epsilon-caprolactone and copolymers thereof, and other polyesters like polybutylene succinate, polybutylene terephtalate adipate, during the melting (up to 300° C.) in a co-rotating twin-screw extruder (Brabender, or the like), in the absence or in the presence of plasticizers. Thus, there are obtained products in the form of film having features of improved applicability in the biomedical and the packaging field.

Spray-dried chitin nanofibrils may easily be added to any biodegradable polymer for medical use, and also to semisynthetic polymers like the polylactic and polyglycolic acid, or hydroxyethyl cellulose or dibutyryl chitin. The latter easily forms transparent, mechanically resistant and biocompatible films, it being soluble in various organic solvents like methanol, ethanol, acetone, chloroform, etc. The presence of dibutyryl chitin in ethanol prevents any disturbance to the spray-dried chitin nanofibrils, so much so that they easily disperse in the dibutyryl chitin solutions. Solvent evaporation yields white films firmly adhering to many materials, like steel, plastics of various nature, glass, wood, paper, etc.

The spray-dried chitin nanofibrils may easily be added also to aqueous solutions of natural polymers, preferably cationic and neutral ones, such as chitosan or chitosan glycolate, or to any biodegradable polymer for medical use and also to semisynthetic polymers like hydroxyethyl cellulose or dibutyryl chitin, or polylactic and polyglycolic acids, the latter two when already polymerized or under polymerization. Dibutyryl chitin, by being soluble in several organic solvents like methanol, ethanol, easily forms transparent, mechanically resistant and biocompatible films.

Lastly, the nanofibrils of the invention may be adsorbed on natural yarns, like wool, cotton, flax, silk (tel quel and regenerated), hemp, jute, for preparing fabrics with antiallergic characteristics typical of chitin. Absorption on yarn surface occurs either through immersion in colloidal suspensions of nanofibrillar chitin or by spray treatment of the yarns or the fabrics themselves.

Chitin Nanofibrils with Silver and Other Metals, Transition Metal Chelation.

Presence of minimum amounts of metallic silver is known to afford antimicrobial activity to various materials. It has surprisingly been found that the silver ion attaches onto the chitin nanofibrils, remaining thereon even after chemical reduction. In example 6 there are adopted conditions and silver concentrations high enough to display its presence by means of a deep black colour, however in practical applications it is not necessary to apply enough silver to blacken the sample; in fact, antimicrobial properties associable to silver are such as to give merely a pearly hue. Chitin nanofibrils adsorb silver ion, which collapses their suspension. This is not obvious, so much so that chromium trichloride does not precipitate the suspensions (violet colour), whereas copper sulfate aggregates the nanofibrils without having them colouring appreciably. Applications of this aspect comprise the chelation of metals, in particular transition ones, for the scopes that are evident to those skilled in the art, such as the recovery of precious metal traces, the elimination of metal traces from polluted environments, the preparation of materials for electronics and nanotechnologies, etc., it being evident that the performances of chitin in the nanofibrillar form are exceptionally better than those described on this subject for commercial raw chitin.

Suspensions of Chitin Nanofibrils in Solutions of Biologically Active Compounds

Some inorganic salts and some organic compounds have the property of aggregating spray-dried chitin nanofibrils, as indicated above, whereas other compounds do not influence the dispersion state of spray-dried chitin nanofibrils. A significant case is that of aqueous solutions of alpha-amino acids, ubiquitous in living systems, or of beta-amino acids or derivatives thereof, like taurine, or of organic solutions of carotenoids, like lutein, them also present in animals and vegetables.

Suspensions of spray-dried chitin nanofibrils containing the above-indicated substances can generate, by aqueous phase evaporation, mechanically resistant films.

These films may be added, e.g., with glycine, thereby performing an intense rehydrating activity if used as cosmetic beauty masks, or be pre-treated with bactericides and fungicides, generating films useful for several medical uses.

EXAMPLES

Example 1

Nanofibrils Preparation by Spray-Drying 10 g Katakura chitin are placed in a flask containing 0.3 M HCl (300-800 ml). Content of the condensing section-equipped flask is boiled for 90 min. During cooling, chitin settles on flask bottom; this facilitates the removal, by means of a pump, of HCl in excess (about 200-600 ml, containing no chitin after dialysis).

From the flask, the chitin and the scarce hydrochloric supernatant are poured into a glass, reconstituting their initial volume of 300-800 ml with water. This suspension is dialyzed for 20 hours against water: three changes of water, initial weight: 845 g; final weight: 873 g; final pH of 3.3, become 4.2 after water addition. This suspension is centrifuged at 3000 rpm to sediment large-sized chitin particles: the supernatant containing the nanofibrils in suspension is sent to the spray-dryer by means of a peristaltic pump. The chitin particles are instead recovered with fresh 3 M hydrochloric acid and treated again.

Operative conditions of Buchi Mini-90 spray-dryer: compressed air supply: 500; heating: 9; inlet temperature: 148° C.; outlet temperature: 87° C.; peristaltic pump flow rate: 400 ml/hour (for these conditions flow cannot be greater). Cover temperature: 42° C.; collection vessel temperature: 36° C.

Example 2

Formulation of Nanofibrils with Chitosan Glycolate and Sodium Hydroxymethylglicinate, and/or Sodium Glycinate Sodium hydroxymethylglycinate (50%) is an antimicrobial useful for cosmetic formulations, produced by Sutton, N.J., USA (CAS no 70161-44-3).

0.3 M HCl (5.5 ml) is added to 50% sodium hydroxymethylglicinate (10 ml) to adjust its pH, which from 11 becomes 7 (neutral hydroxymethylglicinate).

Chitosan powder (3 g) is wetted in 45 ml water, and glycolic acid (1368 mg) is added. This solution is divided into 6 aliquots of about 7.5 g (each one containing 0.5 g chitosan, 7.5 ml water and 228 mg glycolic acid).

1) To the first aliquot of chitosan glycolate it is added neutral hydroxymethylglycinate (85 microliters) prediluted in water (2.5 ml); final pH of 4.5.

2) To the second aliquot it is added neutral hydroxymethylglycinate (170 microliters) prediluted in water (2.5 ml); final pH of 4.8.

3) To the third aliquot it is added neutral sodium glycinate (170 microliters) presolubilized in water (2.5 ml); final pH of 4.8

4) To the fourth aliquot it is added neutral hydroxymethylglycinate (255 microliters) prediluted in water (2.5 ml); final pH of 5.0.

5) To the fifth aliquot there are added nanofibrils (100 mg) suspended in water (2.5 ml), then neutral hydroxymethylglycinate (85 microliters); final pH of 4.5.

6) To the sixth aliquot there are added nanofibrils (100 mg) suspended in water (2.5 ml), then neutral sodium glycinate (85 microliters); final pH of 4.5.

It can be observed that aliquots 1, 5 and 6 gelled rapidly and achieved the same consistency; no difficulties were experienced in dispersing the nanofibrils in the presence of chitosan glycolate, and at about 26° C. no undesirable effects such as syneresis or aggregation were observed at +3 months.

Aliquots 2, 4 and 6 achieved higher consistency with respect to 1, 3 and 5. However, 1 and 5 contained hydroxymethylglycinate in a concentration recommended for antimicrobial activity, whereas the others contained an excess thereof.

Aliquots 3 and 6, produced from sodium glycinate, carry out a low antimicrobial activity. On the contrary, they carry out an intense bactericidal-fungistatic activity if added with 0.4% chlorhexidine hydrochlorate.

Moreover, aliquot 3 is the most suitable for the manufacturing of a spray product, above all if added also with microbicides, like, e.g., chlorhexidine.

In short, it was observed that neutral hydroxymethylglicinate has the ability to gel chitosan glycolate solutions, presumably thanks to new hydrogen bonds between the components, with no local precipitation of the chitosan (not even transitorily). According to the producer, neutral or slightly acid hydroxymethylglicinate has the same antimicrobial abilities of the original one at a pH of 11. The gel under 5) is also advisable for a ready administration of chitosan and chitin to wounds, even bleeding ones, to induce hemostasis and regeneration of injured tissues, as is also that at 3) if used as a spray product. Aliquots 3 and 6 (as spray and as gel, respectively) added with 0.4% chlorhexidine hydrochlorate are active both on gram+ and gram− bacteria and on fungi, besides carrying out an intense tissue healing and repairing activity.

Example 3

Dibutyril Chitin-Based Semisynthetic Polymers with Chitin Nanofibrils

A clear colourless solution is prepared by mere mixing of dibutyryl chitin (36 mg) into ethanol (2 g). This solution is evaporated in a glass Petri dish, yielding a transparent and mechanically resistant film of 2.5 cm in diameter. Analogous solution is added with spray-dried chitin nanofibrils (20 mg), immediately yielding a suspension that does not settle within the time interval required for preparing the film: this suspension is evaporated in a Glass Petri dish, yielding a white and mechanically resistant film of 2.5 cm in diameter. The same operation attempted with lyophilized chitin nanofibrils does not succeed, as it is impossible to obtain a suspension.

Example 4

Semisynthetic Polymers with Chitin Nanofibrils: Hydroxyethyl Cellulose and Other Types of Thickeners Hydroxyethyl cellulose is available in several presentations: for this application it was selected the one marketed as Tylose H-10000-P2, produced by Clariant GmbH, widely used in cosmetic formulations. Chitin nanofibrils (2.5 g) obtained as above were placed in water (40 ml); it was added said hydroxyethyl cellulose (2.0 g), bringing the temperature to 40° C. for 20 min, under gentle stirring. A consistent white gel was obtained, stable even at +5 months, i.e., without neither syneresis nor microbial growth, easily spreadable, with fair mucoadhesiveness, which rapidly dries on-skin, becoming transparent.

Example 5

Natural Polymers with Chitin Nanofibrils: Chitosan

Crustacean chitosan powder (0.5 g) is suspended in water (7.5 ml), and to the suspension it is added glycolic acid (0.23 mg), obtaining a clear solution. A suspension of spray-dried chitin nanofibrils (102 mg) in water (2.5 ml) is added thereto, obtaining a viscous homogeneous suspension, from which incorporated air is removed by negative pressure. This suspension is placed, on a Petri dish, in a stove at 40° C. to evaporate the water, obtaining a chitosan film incorporating spray-dried chitin nanofibrils.

Example 6

Chitin Nanofibrils with Silver Ion or Metallic Silver

Chitin nanofibrils (151 mg) were added to aqueous silver acetate (11 mg in 25 ml water): at +3 hours, sediment was ultracentrifuged, abundantly washed with water (step repeated twice). The following assays were performed with sodium boron hydride, capable of reducing silver ion to zerovalent state: (a) supernatant, pale yellow colour; (b) silver acetate solution, black colour; (c) nanofibrils after ultracentrifugations and washings, dark green colour; (d) control solution, containing silver acetate and nanofibrils, black colour. The silver ion, once reduced to metallic silver, remains adsorbed on the nanofibrils.

Example 7

Suspension of Chitin Nanofibrils in Aqueous Taurine Solution

A clear colourless solution of taurine (sulphurised beta-amino acid) (100 mg) in water (5 ml) is prepared, to which it is added a suspension of spray-dried chitin nanofibrils (100 mg) in water (2.5 ml), obtaining an uniform suspension that does not settle.

Example 8

Suspension of Chitin Nanofibrils in Alcohol Solution of Lutein

A clear, orange/red dyed (carotenoid, xanthophyll dye and antioxidant) lutein (100 mg) solution in ethanol (5 ml) is prepared, to which spray-dried chitin nanofibrils (100 mg) are added, obtaining an uniform suspension that does not settle. Likewise when lutein dissolved in oils like thymol and carvacrol is used.

BIBLIOGRAPHY

1) Belamie E, Davidson P, Giraud-Guille M M. Structure and chirality of the nematic phase in alpha-chitin suspensions. Journal of Physical Chemistry. B, 108, 14991-15000, 2004.
2) Giraud-Guille M M, Belamie E, Mosser G. Organic and mineral networks in carapaces, bones and biomimetic materials. Comptes Rendus Palevol, 3, 503-513, 2004.
3) Jollès P, Muzzarelli R A A. Chitin and Chitinses. Birkhauser, Basel, 1999.
4) Li J, Revol J F, Naranjo E, Marchessault R H. Effect of electrostatic interaction on phase separation behavior of chitin crystallite suspensions. International Journal of Biological Macromolecules, 18, 177-187, 1996.
5) Li J, Revol J F, Naranjo E, Marchessault R H. Effect of the degree of deacetylation of chitin on the properties of chitin crystallites. Journal of Applied Polymers Science, 65, 373-380 (1997).
6) Lu Y, Weng L, Zhang L. Morphology and properties of soy protein isolate thermoplastics reinforced with chitin whiskers. Biomacromolecules, 5, 1046-1051, 2004.
7) Morin A, Dufresne A. Nanocomposites of chitin whiskers from Riftia tubes and poly(caprolactone). Macromolecules, 35, 2190-2199, 2002.
8) Muzzarelli R A A. Chitin, Pergamon. Oxford, 1977.
9) Nair K G, Dufresne A. Crab shell chitin whisker reinforced natural rubber nanocomposites. 1. Processing and swelling behavior. Biomacromolecules, 4, 657-665, 2003a.
10) Nair K G, Dufresne A. Crab shell chitin whiskers reinforced natural rubber nanocomposites. 2. Mechanical behavior. Biomacromolecules, 4, 666-674, 2003b.
11) Nair K G, Dufresne A. Crab shell chitin whiskers reinforced natural rubber nanocomposites. 3. Effect of chemical modification of chitin whiskers. Biomacromolecules, 4, 1835-1842, 2003c.
12) Paillet M, Dufresne A. Chitin whisker reinforced thermoplastic nanocomposites. Macromolecules, 19, 6527-6530, 2001.

13) Persson J E, Domard A, Chanzy H. Single crystals of alpha chitin. International Journal of Biological Macromolecules 14, 221-224, 1992.
14) Revol J F, Li J, Godbout L, Orts W J, Marchessault R H. Chitin crystallite suspension in water: phase separation and chiral nematic ordering. In Advances in Chitin Sciences, A. Domard, C. Jeuniaux, R. A. A. Muzzarelli and G. Roberts, eds., Jacques André, Lyon. 1996. p. 355-360.
15) Revol J F, Marchessault R H. In vitro chiral nematic ordering of chitin crystallites. International Journal of Biological Macromolecules 15, 329-335, 1993.
16) Sriupayo J, Supaphol P, Blackwell J, Rujiravanit R. Preparation and characterization of alpha-chitin whisker-reinforced poly(vinyl alcohol) nanocomposite films with or without heat treatment. Polymer 46, 5637-5644 (2005).

The invention claimed is:

1. Spray-dried chitin nanofibrils characterized by a crystallization water content ranging from 5% to 10% and an hydration state ranging from 10% to 15%, which are capable of instantaneously dispersing in water and of forming stable suspensions in an aqueous or organic medium, and having an IR spectrum containing a sequence of distinctly resolved small bands in the 3855-3652 $cm^{-1}$ range, indicating the hydration state, distinctly resolved bands at 1204 $cm^{-1}$, 975 $cm^{-1}$, and 917 $cm^{-1}$ and distinctly resolved bands at 1656 $cm^{-1}$ and 1622 $cm^{-1}$.

2. The spray-dried chitin nanofibrils according to claim 1, having a X-diffraction spectrum containing evident and distinctly resolved peaks at 0.962 nm, 0.704 nm, 0.468 nm and 0.344 nm.

3. A stable suspension of chitin nanofibrils according to claim 1 in an aqueous or organic medium.

4. The suspension according to claim 3, comprising further components selected from the group consisting of thickeners, plasticizers, bactericides, fungicides, antimicrobials, metal ions, alpha-amino acids, beta-amino acid, carotenoids, moisturizers, derivatives and mixtures thereof.

5. The spray-dried chitin nanofibrils according to claim 1, having an average length of about 250 nm.

6. A composition comprising the chitin nanofibrils according to claim 1 in a form selected from the group consisting of dry state, aqueous or organic liquid suspension, gel, paste and a pharmaceutically or cosmetically acceptable excipient.

7. The composition according to claim 6, comprising further components selected from the group consisting of thickeners, plasticizers, bactericides, fungicides, antimicrobials, metal ions, alpha-amino acids, beta-amino acids, carotenoids, moisturizers, derivatives and mixtures thereof.

8. An article selected from the group consisting of films, sponges, and synthetic or natural fabric, comprising thereinside or adsorbed on its surface the chitin nanofibrils according to claim 1.

9. A container comprising the chitin nanofibrils according to claim 1, equipped with means for intra/subcutaneous or topical application selected from the group consisting of hypodermic syringes, spray cans, nebulizers, pencils, brushes and other means capable of depositing on-skin a liquid thin layer, which generates a film of protective and reabsorbable material.

10. A fiber, fabric or film incorporating the chitin nanofibrils according to claim 1 and having synthetic or semi-synthetic nature.

11. The fiber, fabric or film according to claim 10, comprising further a biologically active substance.

12. The fiber, fabric or film according to claim 10 obtainable through a process comprising mixing of the chitin nanofibrils, and optionally the biologically active substance, to a polymer mass during heating and melting and subsequent spinning, extrusion or hot-forming.

13. Natural yarn or fabric treated with the chitin nanofibrils according to claim 1.

14. The yarn or fabric according to claim 13, further comprising a biologically active substance attached onto the chitin nanofibrils.

15. A method of protective or curative treatments of abrasions, wounds, cutaneous burns, or treatments for supporting and stimulating haemostasis, healing and regeneration processes of injured tissues comprising applying the chitin nanofibrils of claim 1.

16. A method of dermocosmesis treatments comprising applying the chitin nanofibrils of claim 1 through subcutaneous hypodermic injection thereof or cutaneous application with masks, films, or sponges.

17. A method comprising mixing the chitin nanofibrils of claim 1 as metal ion chelating agents or as slow-release agents of drugs with a biologically active substance.

* * * * *

UNITED STATES PATENT AND TRADEMARK OFFICE
CERTIFICATE OF CORRECTION

PATENT NO. : 8,552,164 B2  Page 1 of 1
APPLICATION NO. : 12/094912
DATED : October 8, 2013
INVENTOR(S) : Morganti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1219 days.

Signed and Sealed this

Fifteenth Day of September, 2015

Michelle K. Lee
*Director of the United States Patent and Trademark Office*